United States Patent [19]
Hartmann

[11] 3,997,466
[45] Dec. 14, 1976

[54] METALLIC FOIL COATED WITH SCANDIUM TRITIDE FOR USE AS A BETA PARTICLE SOURCE IN AN IONIZATION DETECTOR AT HIGH TEMPERATURES AND METHOD OF MANUFACTURE

[75] Inventor: Charles H. Hartmann, Moraga, Calif.

[73] Assignee: Varian Associates, Palo Alto, Calif.

[22] Filed: Sept. 10, 1973

[21] Appl. No.: 395,498

Related U.S. Application Data

[63] Continuation-in-part of Ser. No. 232,016, March 6, 1972, abandoned.

[52] U.S. Cl. .................... 252/301.1 R; 73/23.1; 75/122.5; 148/20.3; 423/249
[51] Int. Cl.[2] .......................................... C21D 1/76
[58] Field of Search ............ 252/301.1 R; 75/122.5, 75/134 R, 175.5; 250/375, 381, 384, 304; 423/249; 148/20.3; 427/5, 250, 295; 73/23.1

[56] References Cited
UNITED STATES PATENTS

| | | | |
|---|---|---|---|
| 3,185,845 | 5/1965 | Lively et al. | 250/304 |
| 3,601,609 | 8/1971 | Yauger | 250/375 |
| 3,716,491 | 2/1973 | Yannopoulos | 75/122.5 X |

FOREIGN PATENTS OR APPLICATIONS 1,164,398   9/1969   United Kingdom

OTHER PUBLICATIONS

Kahn, L. et al. The Emanation of Tritium from Two Electron–Capture Detectors. In J. of Gas Chrom. Aug., 1965, pp. 287–288.
Shoemake, G. R. et al, The Effect of Temperature and Carrier Gas on the Loss Rate of Tritium from Radioactive Foils, In J. of Chrom. vol. 12 pp. 314–320 (1963).

*Primary Examiner*—Richard E. Schafer
*Attorney, Agent, or Firm*—Stanley Z. Cole; Gerald M. Fisher; John J. Morrissey

[57] ABSTRACT

A metallic foil coated with scandium tritide is treated so as to manifest a legally acceptable tritium emanation rate at temperatures above 225° C, thereby becoming usable as a beta particle emitter is ionization detectors such as electron capture detectors or the like operated at high temperatures. The treatment includes heating the foil for a length of time sufficient to cause the foil's tritium emanation ratio to reach a value which corresponds to a legally acceptable emanation ratio for the foil at selected operating temperatures above 225° C.

27 Claims, 4 Drawing Figures

| PLATINUM FOIL APPROXIMATELY 3/1000" THICK | → | SPUTTER 800 Å SCANDIUM | → | OUTGAS IN VACUUM @ 350°C - 400°C 4 HOURS | → |

| → | MAINTAIN TEMPERATURE AND ADMIT TRITIUM 1 HOUR | → | VENT CHAMBER AT 300°C UNTIL EMANATION RATIO REDUCES TO 0.16 (APPROXIMATELY 14 HOURS) |

METALLIC FOIL COATED WITH SCANDIUM TRITIDE FOR USE AS A BETA PARTICLE SOURCE IN AN IONIZATION DETECTOR AT HIGH TEMPERATURES AND METHOD OF MANUFACTURE

BACKGROUND OF THE INVENTION

This application is a continuation-in-part of Ser. No. 232,016 filed Mar. 6, 1972 now abandoned.

Certain types of ionization detectors in which gaseous matter to be analyzed is ionized within a cell sample utilize a radiation source producing beta emission for the ionization of the sample. Such beta emitters are required in electron capture detectors and helium ionization detectors which are used in the field of gas chromatography.

These detector cells contain a radioactive source such as $Ti^3H$ or $^{63}Ni$ as the internal beta emitter. The $^{63}Ni$ beta emitter has a higher emitter activity and a higher cost than the well known $Ti^3H$; and although the higher activity results in higher sensitivity with a smaller linear range, it has a distinct advantage at elevated temperatures.

As explained in U.S. Pat. No. 3,601,609, issued Aug. 24, 1971 to W. L. Yauger, entitled "Ionization Detection Device Using a Nickel $^{-63}$ Radioactive Source", the United States Atomic Energy Commission has limited the operating temperature of detectors using tritiated foils to ranges below 220°–225° C because tritium emanation from such foils reaches unacceptable levels above this temperature range. However, for certain applications, operation at temperatures below 220° C causes chronic contamination of the source by condensation. This contamination is very deleterious because beta particles are low energy ionizers and any obstruction to their radiation will seriously inhibit the radioactive ionization of the sample gases. To avoid this contaminating condensation, it is desirable to operate at temperatures above 250° C, for example at 350° C. This higher temperature operation is permitted by the AEC with the expensive $^{63}Ni$ beta emitters whereas the use of tritiated emitters at such temperatures has been forbidden heretofore due to their excessive tritium emanation.

In the present invention, a novel process is described for manufacturing and treating tritiated metallic foils for use as beta emitters in such ionization detectors. These treated foils will exhibit acceptable emanation levels at elevated operating temperatures, i.e. greater than 250° C. The process of manufacturing radioactive foils having tritium emanation levels is as follows.

Platinum or stainless steel foils coated with scandium are placed in a vessel. The vessel is heated and evacuated to drive off undesired adsorbed gases. Tritium is then admitted into the vessel and is absorbed or otherwise captured by the coated foils. The tritium gas may then be removed from the atmosphere surrounding the foils by various means, e.g. venting, reacting or purging. The temperature is not critical during the purging step but preferrably is maintained at an intermediate value until the excess radioactive material is removed or immobilized.

The process of treating a tritiated radioactive foil having a tritium emanation rate in excess of the legally allowable value at elevated temperatures comprises the step of preliminarily heating the tritiated foil, under controlled radiation precautions, at an elevated temperature above 250° C, for example at 300° C, for a sufficient time, for example 2 to 16 hours, to drive off the excess radioactive material (i.e., tritium) until such time as the tritium emanation rate falls to an acceptable radiation level. Since the AEC has decreed that the tritium emanation rate from a standard 250 mCi $Ti^3H$ source at or below 200° C is acceptable, this emanation rate can conveniently be employed as a standard emanation level. Thus the emanation ratio of a tritiated foil, which is defined as the ratio of the measured tritium emanation rate of that foil to the tritium emanation rate of a standard 250 mCi $Ti^3H$ source at 220° C, is a simple dimensionless number for comparing the tritium emanation levels of various tritiated beta sources, with emanation ratios of 1 or less being within the accepted standards of the AEC.

DESCRIPTION OF THE PREFERRED EMBODIMENTS

Figure 1:
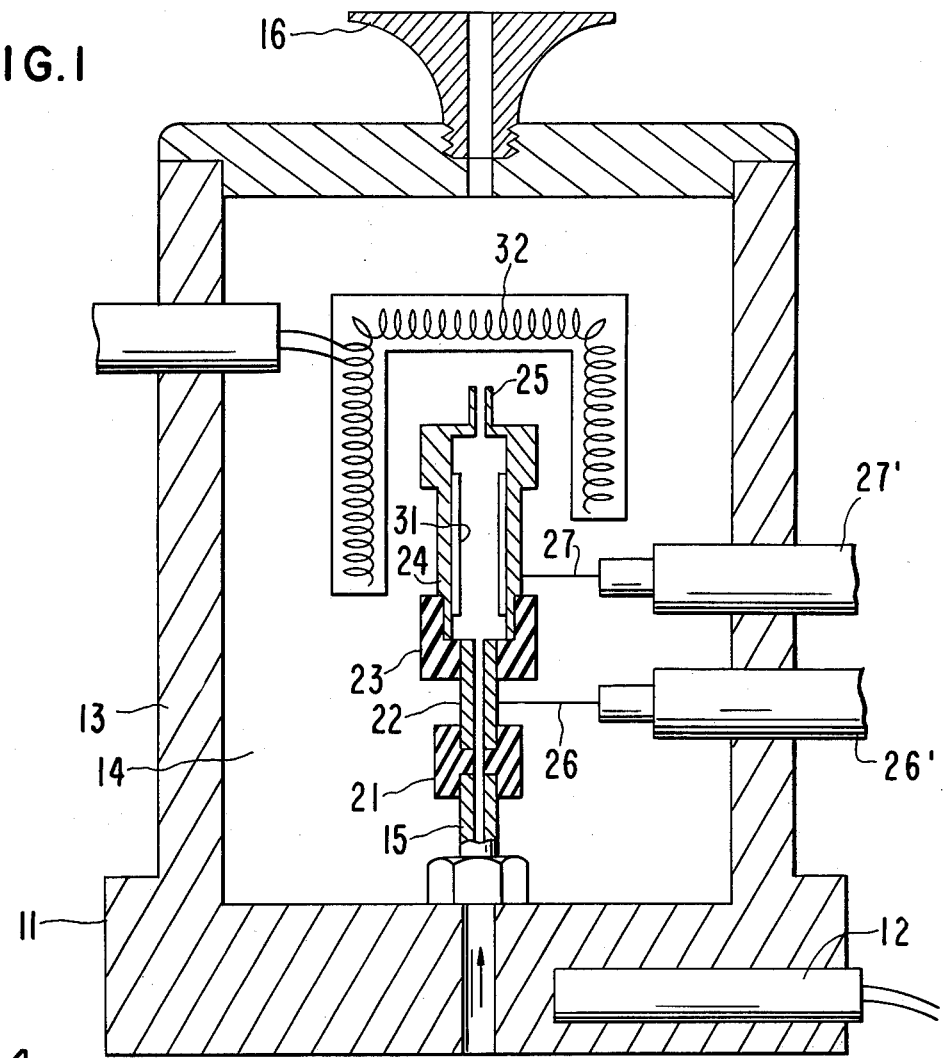
FIG. 1 is a longitudinal cross-section view of an electron capture detector utilizing the novel beta radiation source of the present invention.

Referring now to the drawing, the electron capture detector assembly shown in FIG. 1 comprises a mounting base 11 having a base heater 12 therein and a body envelope 13 surrounding the chamber 14 in which the detector cell is mounted. The cell comprises a hollow stainless steel input tubing 15 mounting the cell on the base 11 and through which the gas to be analyzed is introduced into the cell.

A first hollow cylindrical ceramic tubing 21 is vacuum sealed at one end to the inner end of the input tubing 15, and vacuum sealed at the other end to a hollow cylindrical stainless steel tube 22 forming the collector electrode or anode. A second hollow cylindrical, cup-shaped ceramic tubing 23 is vacuum sealed to the other end of the collector electrode 22 and is also vacuum sealed to the lower end of a hollow cylindrical stainless steel polarization electrode or cathode 24. The upper end of the polarization electrode 24 is provided with an exhaust tubing 25.

Electrical leads 26 and 27 extend through suitable insulators 26' and 27' in the side of envelope 13 and couple to the associated collector and polarization electrodes for providing the desired steady state or pulsed DC potential in the range of 0 to 90V across the anode and cathode electrodes during use.

A tritiated foil 31 is positioned around the inner wall of the polarization electrode 24. A heater coil 32 is mounted on the body envelope 13 and extends around the polarization electrode portion of the detector cell for raising the temperature of this reaction region of the cell to the desired operating temperature, for example 250°–350° C. The chamber is vented through a combination handle and vent 16.

In operation of the electron capture detector with the output from a gas chromatograph, beta emission from the radiation source 31 results in an ionization of the carrier gas, either $N_2$ or Ar plus about 10 percent methane quenching gas, to form an electron flow in the detector cavity in the order of $10^{-8}$ amps. The background current or standing current formed by the electrons collected by the relatively weak field strength of the potential across the anode and cathode. Those substances in the gas which have an affinity for free electrons deplete the standing current as they pass through the cell from input to exhaust. The magnitude of the current depletion is a measure of the amount of capturing species in the detector, and is also a measure of the electron affinity of the species.

Tritiated foil has been widely used in the past as the radioactive source for ionization detectors (usually a standard 250 mCi $^3H$). The tritium, would typically be occluded in a suitable substrate, usually titanium, plated on a stainless steel foil. When operated at high temperatures, for example above 220° C, the untreated $Ti^3H$ produces an unacceptable level of tritium emanation as determined by the U.S. Atomic Energy Commission, where emanation refers to the release rate of the tritium gas expressed in its radioactive equivalent, typically $2\mu ci/min$. However, often it is desired to operate above 220° C to prevent contamination of the radioactive source as stated above, and for this reason $^{63}Ni$ had been previously required for such high-temperature operation.

Figure 2:
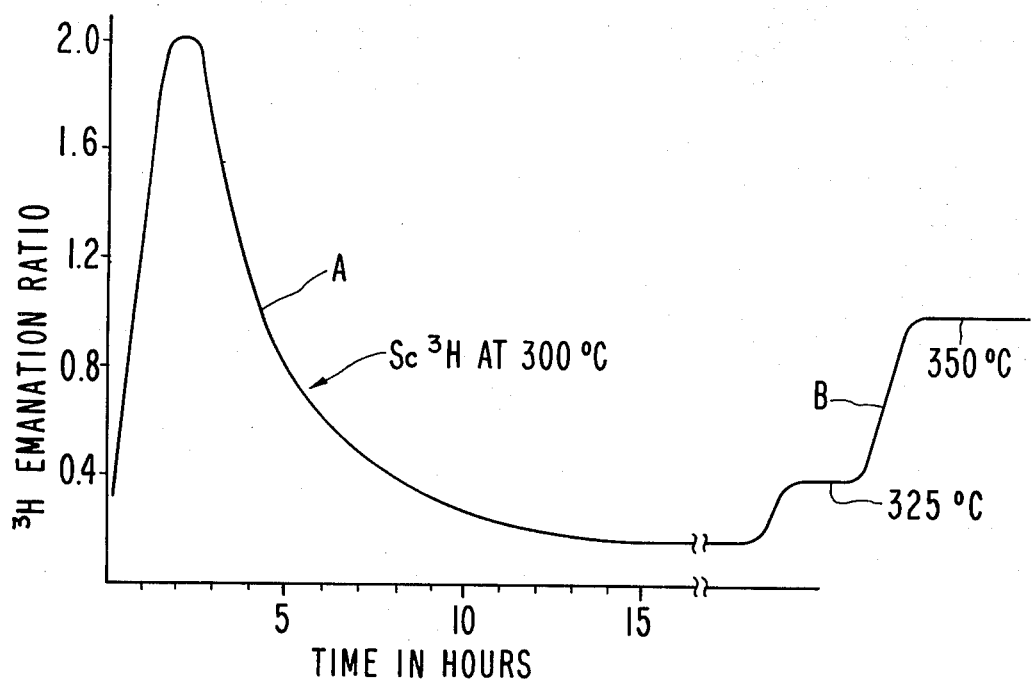
FIG. 2 illustrates a method by which a $Sc^3H$ beta radiation source was brought, by heat treatment, to a safe tritium emanation level.

It has been discovered that a heat treatment will condition a scandium tritide coated foil so that subsequent operation at other, either higher or lower, temperatures will yield a $^3H$ emanation rate within acceptable limits. For example, and referring to FIG. 2, a scandium tritide foil was obtained from the manufacturer, U.S. Radium Corporation of Bloomsburgh, Penn., specified as 250 mCi of tritium. If this foil were to be placed directly in an electron capture detector without first being heat treated according to this invention, and such detector were to be operated at a relatively high operating temperature, for example 325° C, the tritium emanation therefrom would exceed the legally acceptable level. However, if this foil is first heated at 300° C, the tritium emanation therefrom, as can be seen from the curve A which shows emanation ratio vs. time, will reach a peak value of about 2 at about two hours and then will fall off to a substantial equilibration value of about 0.16 after about 14 hours. After this heat treatment, the same foil may be operated at higher temperature levels without exceeding an acceptable tritium emanation level. This is illustrated by curve B which shows a subsequent operation of this foil at 325° C with an emanation ratio of 0.4, and a still further operation of this foil at 350° C with an emanation ratio of 1. Thus, since one arbitrarily selects 1 as an acceptable emanation ratio, this heat treated foil may be used with operating temperatures up to 350° C.

Figure 3:
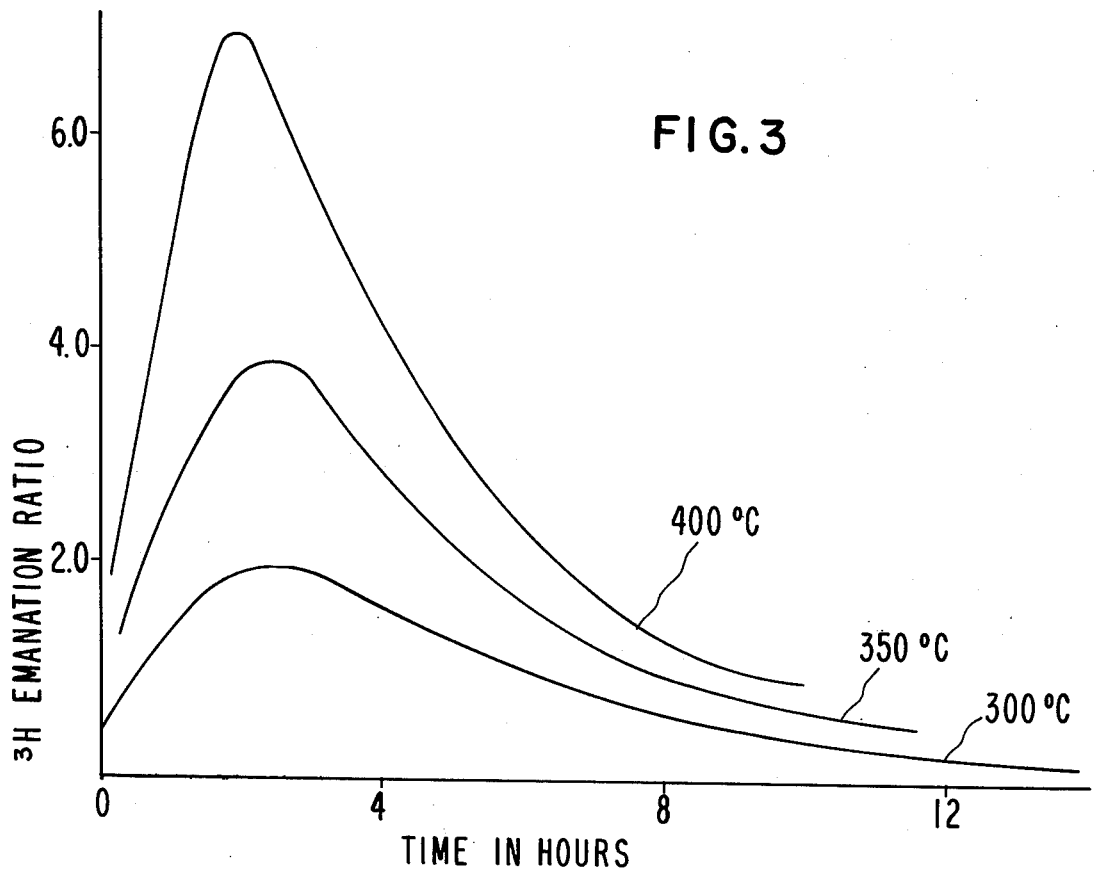
FIG. 3 illustrates the heat treatment of three different beta radiation sources at three different heat treatment temperatures.

Different heat treatments yield different treatment results as illustrated by the curves in FIG. 3 for three different $Sc^3H$ foils. The end points of all three of the treatments illustrated show acceptable emanation ratios. The lower temperature of 300° C required about 14 hours to reach equilibration with relatively low percentage of $^3H$ loss during the process (calculated from the area under the emanation ratio curve). The higher temperature treatment of 400° C required a shorter time to reach equilibration, about 10 hours, but with relatively higher percentage of $^3H$ loss and shorter useable life expectance when the source is actually employed in the detector process of a gas chromatograph.

It is not required that equilibration of the $^3H$ emanation be reached before terminting the process. The source will be useable in terms of acceptable $^3H$ emanation ratios whenever the tritium emanation rate drops below the acceptable emanation ratio such as 1. In addition, it is not necessary to continue the heat treatment at a particular temperature, for example 400° C, until the selected acceptable emanation ratio is reached, provided that the foil in use is to be operated at a lower temperature, for example 350° C, at which operating temperature the acceptable emanation ratio is not exceeded.

In a process for producing tritiated radiation sources, the foils can be obtained from the manufacturer with a specified amount of occluded tritium, i.e., 250 mCi, 500 mCi, 1000 mCi, etc. Each foil is inserted in a detector cell in a manner similar to the foil 31 in cell 21, 22, 23, 24, 25 of FIG. 1. Groups of cells are connected to a purging gas source at 21 and to a venting manifold 25 and placed in a chamber. The chamber is then heated to a suitable elevated temperature, for example, 300°–320° C, and left overnight, for example, 16 hours.

After this treatment, the tritium emanation level of the foils will have decayed to below the acceptable emanation ratio, which correlates to the arbitrarily set acceptable ratio of 1 at the desired upper limit operating temperature for the foils, for example, 340° C. The foils are then installed in the individual electron capture detectors during final assembly, and a spot check is made to determine the actual tritium emanation rate at the upper intended temperature of operation of the detectors.

Figure 4:
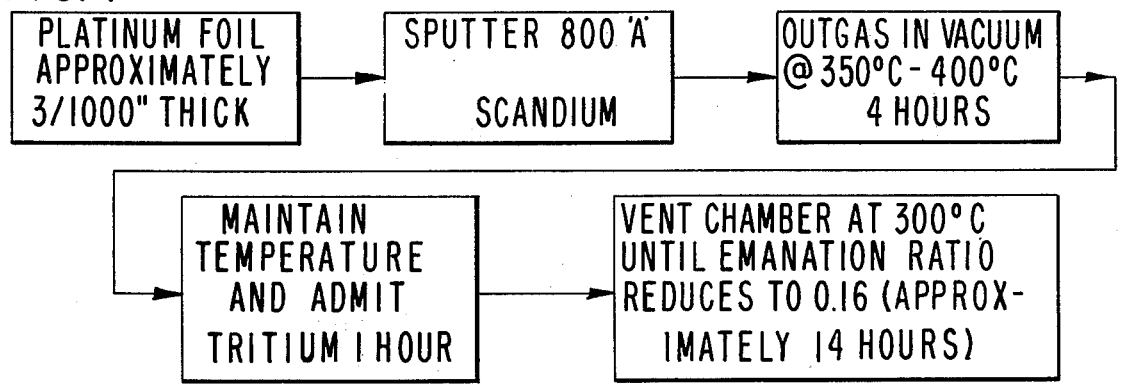
FIG. 4 is a flow chart illustrating the manufacture of tritiated foils having acceptable emanation ratios at high operating temperatures.

With reference to FIG. 4, it is also possible to manufacture tritiated which exhibit an acceptable $^3H$ emanation rates at high operating temperatures. Platinum or stainless steel foils approximately 0.003 inch thick are sputtered with scandium to a thickness of approximately 800A. The foils are then placed in a heatable vacuum chamber and heated to 350° to 400° C under vacuum to outgas the chamber and foils. These conditions of temperature and pressure are maintained for four hours. The temperature is maintained while tritium gas is introduced into the chamber. This temperature and atmosphere is maintained until the foils are saturated with tritium. The excess tritium is removed and the chamber is allowed to cool to 300° C. These conditions are maintained until tritium emanations from the foils fall to an equilibrium value of emanation ratio of about 0.16. This condition is illustrated by curve B, FIG. 2, which shows the emanation ratio for operation at 325° C and 350° C, respectively at 0.4 and 1.0. These foils can now be operated at temperatures greater than 225° C without exceeding an emanation ratio of 1.

If during the manufacture of the foils the temperature of the chamber after the removal of the excess tritium is maintained at 400° C, or 350° C, or 300° C, the emanation ratio decline is that shown for the corresponding curves in FIG. 3.

Thus it can be seen that foils can be manufactured by this process which do not exceed the AEC tritium emanation limits even though operated at temperatures in excess of 225° C.

What is claimed is:

1. A method of treating a scandium-coated foil for use as a beta-particle emitter at temperatures above 225° C, said method comprising:

a. an outgassing step, which comprises:

1. inserting said scandium-coated foil into an evacuable and heatable chamber;
2. evacuating said chamber; and
3. heating said chamber while continuing to evacuate said chamber to remove therefrom undesired gases outgassed by said foil; and b. a tritiating step, which comprises:
1. discontinuing the evacuation of said chamber;
2. introducing tritium into said chamber; and
3. providing a constant chamber temperature at least until the tritium equilibrates with said foil; and c. a calibrating step, which comprises:
1. reducing the partial pressure of tritium in said chamber; and
2. adjusting the chamber temperature to heat said foil at a treatment temperature above 250° C until the emanation ratio of said foil at said treatment temperature changes to a first predetermined value which correlates to a second predetermined value for the emanation ratio of said foil at an operating temperature which is different from said treatment temperature, said second predetermined value for the emanation ratio of said foil being an acceptable emanation ratio value.

2. A heating process for treating a beta-particle source, said source comprising a tritiated scandium surface portion and initially having an unacceptable tritium emanation rate at a desired high operating temperature, wherein said source after being so treated exhibits an acceptable tritium emanation rate at said desired high operating temperature, said process comprising the steps of:
1. inserting said source having an unacceptable tritium emanation rate at said desired high operating temperature into a chamber; and
2. heating said source in said chamber at a treatment temperature above 250° C but below the fusion temperature of said source until the emanation ratio of said source decreases to a predetermined value such that in subsequent operation of said source at said desired high operating temperature said source exhibits an emanation ratio of 1 or less.

3. The process of claim 2 wherein said source comprising a tritiated scandium surface portion is a foil having a scandium tritide ($Sc^3H$) coating.

4. The process of claim 3 wherein said foil comprises a metallic substrate coated with scandium tritide, said substrate being selected from the group consisting of platinum and stainless steel.

5. The process of claim 2 wherein said source is heated in said chamber at a temperature sufficient to produce an emanation ratio of at least 2 prior to the decrease in the rate of tritium emanation from said source to a value corresponding to an acceptable emanation ratio of 1 or less at said desired operating temperature.

6. The process of claim 2 wherein said heating of said source in said chamber is continued until said tritium emanation equilibrates at an emanation ratio of 1 at an operating temperature of at least 300° C.

7. The process of claim 6 wherein said source comprises a foil having a scandium tritide surface portion.

8. The process of claim 7 wherein said foil comprises a metallic substrate coated with scandium tritide ($Sc^3H$), said substrate being selected from the group consisting of platinum and stainless steel.

9. A heating process for treating a beta-particle source, said source comprising a tritiated scandium surface portion and initially having an unacceptable tritium emanation rate at a desired high operating temperature, wherein said source after being so treated exhibits an acceptable tritium emanation rate at said desired high operating temperature, said process comprising the steps of:
1. inserting said source having an unacceptable tritium emanation rate at said desired high operating temperature into a chamber;
2. heating said source in said chamber at a treatment temperature above 250° C but below the fusion temperature of said from said source; and
3. removing said $^3H$ gas from the vicinity of said source, said heating being continued until the emanation ratio of said source decreases to a predetermined value such that in subsequent operation of said source at said desired high operating temperature said source exhibits an emanation ratio of 1 or less.

10. The process of claim 9 wherein said source comprising a tritiated scandium surface portion is a foil having a scandium tritide ($Sc^3H$) coating.

11. The process of claim 10 wherein said foil comprises a metallic substrate coated with scandium tritide, said substrate being selected from the group consisting of platinum and stainless steel.

12. The process of claim 9 wherein said source is heated in said chamber at a temperature sufficient to produce an emanation ratio of at least 2 prior to the decrease in the rate of tritium emanation from said source to a value corresponding to an acceptable emanation ratio of 1 or less at said desired operating temperature.

13. The process of claim 9 wherein said heating of said source in said chamber is continued until said tritium emanation equilibrates at an emanation ratio of 1 at an operating temperature of at least 300° C.

14. The process of claim 13 wherein said source comprises a foil having a scandium tritide surface portion.

15. The process of claim 14 wherein said foil comprises a metallic substrate coated with scandium tritide ($Sc^3H$), said substrate being selected from the group consisting of platinum and stainless steel.

16. The method of producing a beta-emitting radioactive source having an acceptable tritium emanation level from a source comprising a tritiated scandium surface portion that initially exhibits an emanation ratio value of greater than 1 at an operating temperature above 250° C, said method comprising the steps of inserting said source into a heatable chamber and heating said source at a temperature above 250° C but below the fusion temperature of said source while removing said tritium emanation from the atmosphere of said chamber for a length of time sufficient for the emanation ratio of said source to drop to a value no greater than 1.

17. The method of claim 16 wherein said radioactive source comprising a tritiated scandium surface portion is a metallic foil.

18. The method of producing a beta-emitting radioactive source having an acceptable tritium emanation level from a source comprising a tritiated scandium surface portion that initially exhibits an emanation ratio having a value greater than 1 at an operating temperature above 250° C, said method comprising the steps of inserting said source into a heatable and purgeable chamber and heating said source at a temperature above 250° C but below the fusion temperature of said source until said emanation ratio of said source passes through a maximum value.

19. The method of claim 18 wherein said step of heating said source is continued until said emanation ratio reaches a value not greater than 1.

20. The method of claim 19 wherein said radioactive source comprises a foil, said foil comprising a metallic substrate coated with scandium tritide ($Sc^3H$).

21. A tritiated scandium-coated foil for use as a beta-particle source, said foil having an acceptable tritium emanation rate at a desired high operating temperature, said foil being produced by:
1. inserting a tritiated scandium-coated foil having an unacceptable tritium emanation rate at said desired high operating temperature into a heatable chamber;
2. heating said foil at a temperature above 250° C but below the fusion temperature of said foil to drive tritium gas from said foil; and
3. removing said tritium gas from the chamber atmosphere, said heating being continued until the emanation ratio of said foil decreases to a predetermined value such that in subsequent operation of said foil at said desired high operating temperature said foil exhibits an emanation ratio of 1 or less.

22. A heating process comprising the steps of inserting a beta-emitting radioactive source comprising a tritiated scandium surface portion initially having an unacceptable tritium emanation ratio at a desired operating temperature into a purging chamber, heating said source to a temperature above 250° C but below the fusion temperature of said source, and continuing to heat said source while said emanation ratio of said source passes through a maximum emanation ratio value, said process causing said source to exhibit an acceptable emanation ratio at said desired operating temperature.

23. The heating process of claim 22 wherein said beta-emitting radioactive source is a foil having a scandium tritide surface portion.

24. A beta-particle source having an acceptable tritium emanation rate at a desired high operating temperature, said source being produced by a process comprising:
a. an outgassing step, which comprises:
1. inserting an object having a scandium surface portion into a heatable chamber;
2. evacuating said chamber; and
3. heating said chamber while continuing to evacuate same to remove therefrom undesired gases outgassed by said object; and
b. a tritiating step, which comprises:
1. discontinuing the evacuation of said chamber;
2. introducing tritium into said chamber; and
3. providing a constant chamber temperature at least until the tritium equilibrates with said scandium surface portion of said object, thereby causing said object to become a beta-particle source; and
c. a calibrating step, which comprises:
1. reducing the partial pressure of tritium in said chamber; and
2. adjusting the chamber temperature to heat said beta-particle source at a treatment temperature above 250° C but below the fusion temperature of said source until the emanation ratio of said source at said treatment temperature decreases to a first predetermined value which correlates to a second predetermined value for the emanation ratio of said beta-particle source at an operating temperature which is different from said treatment temperature, said second predetermined value for the emanation ratio of said beta-particle source being an acceptable emanation ratio value.

25. The beta-particle source of claim 24 wherein said object having a scandium surface portion is a foil.

26. The beta-particle source of claim 25 wherein said foil comprises a substrate having a scandium coating on at least a portion thereof.

27. The beta-particle source of claim 26 wherein said substrate is a metal selected from the group consisting of platinum and stainless steel.

* * * * *

UNITED STATES PATENT AND TRADEMARK OFFICE
CERTIFICATE OF CORRECTION

PATENT NO. : 3,997,466
DATED : December 14, 1976
INVENTOR(S) : CHARLES H. HARTMANN It is certified that error appears in the above-identified patent and that said Letters Patent are hereby corrected as shown below:

Column 1, line 13: Delete "sample".

Column 1, line 49: After "acceptable" insert --tritium--.

Column 2, line 24: After "different" insert --Sc $^3$H--.

Column 3, line 38: After "and" insert --if--.

Column 4, line 2 : Change "terminting" to --terminating--.

Column 4, line 34: After "tritiated" insert --foils--.

Column 5, line 4 : Change "containuing" to --continuing--.

Column 6, line 14: After "said" (first occurrence) insert --source to drive $^3$H gas--.

Signed and Sealed this

*Twenty-seventh* Day of *June 1978*

[SEAL]

Attest:

RUTH C. MASON
*Attesting Officer*

DONALD W. BANNER
*Commissioner of Patents and Trademarks*